United States Patent
McIntosh et al.

(10) Patent No.: US 7,280,866 B1
(45) Date of Patent: Oct. 9, 2007

(54) NON-INVASIVE SCREENING OF SKIN DISEASES BY VISIBLE/NEAR-INFRARED SPECTROSCOPY

(75) Inventors: Laura M. McIntosh, St. Laurent (CA); Michael Jackson, Winnipeg (CA); Henry Mantsch, II, Winnipeg (CA); James R. Mansfield, Boston, MA (US); A. Neil Crowson, Winnipeg (CA); John W. P. Toole, Winnipeg (CA)

(73) Assignee: National Research Council of Canada, Ottawa, Ontario (CA)

( * ) Notice: Subject to any disclaimer, the term of this patent is extended or adjusted under 35 U.S.C. 154(b) by 343 days.

(21) Appl. No.: 10/089,314

(22) PCT Filed: Oct. 5, 2000

(86) PCT No.: PCT/CA00/01187

§ 371 (c)(1), (2), (4) Date: Aug. 5, 2002

(87) PCT Pub. No.: WO01/24699

PCT Pub. Date: Apr. 12, 2001

Related U.S. Application Data

(60) Provisional application No. 60/157,857, filed on Oct. 6, 1999.

(51) Int. Cl.
A61B 5/00 (2006.01)

(52) U.S. Cl. .................. 600/475; 600/477; 600/562

(58) Field of Classification Search ............... 600/473, 600/475–477, 322, 323, 326, 328, 562–572; 250/339.01, 339.06, 339.12; 436/63, 64, 436/171; 356/301–303
See application file for complete search history.

(56) References Cited

U.S. PATENT DOCUMENTS 4,930,516 A 6/1990 Alfano et al.

(Continued)

FOREIGN PATENT DOCUMENTS

WO WO98/46133 10/1998

OTHER PUBLICATIONS

Sowa et al. "Near-Infrared Spectroscopic Assessment of Tissue Hydration Following Surgery" (1999) Journal of Surgical Research 86: 62-69.*

Primary Examiner—Ruth S. Smith
(74) Attorney, Agent, or Firm—Michael R. Williams; Adrian D Battisan; Ryan W. Dupuis

(57) ABSTRACT

A non-invasive tool for skin disease diagnosis would be a useful clinical adjunct. The purpose of this study was to determine whether visible/near-infrared spectroscopy can be used to non-invasively characterize skin diseases. In-vivo visible- and near-infrared spectra (400-2500 nm) of skin neoplasms (actinic keratoses, basal cell carcinomata, banal common acquired melanocytic nevi, dysplastic melanocytic nevi, actinic lentigines and seborrheic keratoses) were collected by placing a fiber optic probe on the skin. Paired t-tests, repeated measures analysis of variance and linear discriminant analysis were used to determine whether significant spectral differences existed and whether spectra could be classified according to lesion type. Paired t-tests showed significant differences (p<0.05) between normal skin and skin lesions in several areas of the visible/near-infrared spectrum. In addition, significant differences were found between the lesion groups by analysis of variance. Linear discriminant analysis classified spectra from benign lesions compared to pre-malignant or malignant lesions with high accuracy. Visible/near-infrared spectroscopy is a promising non-invasive technique for the screening of skin diseases.

12 Claims, 4 Drawing Sheets

U.S. PATENT DOCUMENTS

| | | |
|---|---|---|
| 5,042,494 A | 8/1991 | Alfano |
| 5,074,306 A | 12/1991 | Green et al. |
| 5,205,291 A | 4/1993 | Potter |
| 5,369,496 A | 11/1994 | Alfano et al. |
| 5,413,108 A | 5/1995 | Alfano |
| 5,596,992 A * | 1/1997 | Haaland et al. ............. 600/473 |
| 5,687,730 A | 11/1997 | Doiron et al. |
| 5,699,797 A | 12/1997 | Godik |
| 5,701,902 A | 12/1997 | Vari et al. |
| 5,747,789 A | 5/1998 | Godik |
| 5,813,403 A * | 9/1998 | Soller et al. ................. 600/310 |
| 5,833,612 A | 11/1998 | Eckhouse et al. |
| 5,836,872 A | 11/1998 | Kenet et al. |
| 5,883,708 A | 3/1999 | Jung et al. |
| 5,961,466 A | 10/1999 | Anbar |
| 5,987,351 A | 11/1999 | Chance |
| 6,008,889 A | 12/1999 | Zeng et al. |
| 6,032,070 A | 2/2000 | Flock et al. |
| 6,070,092 A | 5/2000 | Kazama et al. |
| 6,258,576 B1 * | 7/2001 | Richards-Kortum et al. ....................... 435/40.52 |
| 6,324,417 B1 | 11/2001 | Cotton |
| 6,421,553 B1 * | 7/2002 | Costa et al. ................. 600/476 |
| 6,424,859 B2 * | 7/2002 | Jackson et al. ............. 600/475 |
| 6,671,540 B1 * | 12/2003 | Hochman ................... 600/431 |

\* cited by examiner

NON-INVASIVE SCREENING OF SKIN DISEASES BY VISIBLE/NEAR-INFRARED SPECTROSCOPY

PRIOR APPLICATION INFORMATION

This application is a national phase application of PCT application CA00/01187, filed Oct. 5, 2000 which claims benefit of U.S. Provisional Application 60/157,857, filed Oct. 6, 1999.

FIELD OF THE INVENTION

The present invention relates generally to the field of spectroscopy. More specifically, the present invention relates to a method for non-invasively diagnosing skin diseases using visible and near-infrared spectroscopy.

BACKGROUND OF THE INVENTION

Skin cancer is the most common human cancer. In 1999, it is estimated that there will be 70000 new cases of skin cancer in Canada (Canadian Cancer Statistics: Toronto: National Cancer Institute of Canada, 1999) and more than 1 million new cases in the United States. The clinical diagnosis is often difficult since many benign skin diseases resemble malignancies upon visual examination. As a consequence, histopathological analysis of skin biopsies remains the standard for confirmation of a diagnosis. However, the decision must be made as to which and how many suspicious skin diseases to biopsy.

A rapid, non-invasive technique that could be utilized for characterization of skin diseases prior to biopsy would be useful. Visible/infrared (IR) spectroscopy may be that tool (Jackson et al, 1997, *Biophys Chem* 68:109-125). The IR spectrum is divided into three regions: near-IR (700-2500 nm), mid-IR (2500-50000 nm) and far-IR (beyond 50000 nm). As light in the far-IR region is completely absorbed by tissues, it is of little use for tissue analysis. Mid-IR light is absorbed by a variety of materials in skin, thus providing an insight into skin biochemistry. We have shown that biopsies from basal cell carcinoma (BCC), squamous cell carcinoma (SCC) and melanocytic tumors have distinct mid-IR signatures when compared to normal skin (McIntosh et al, 1999, *J Invest Dermatol* 112:951-956; McIntosh et al, 1999, *Biospectroscopy* 5:265-275; Mansfield et al, 1999; *Appl Spectroscopy*, 53:1323-1330). However, the diagnostic potential of mid-IR spectroscopy in-vivo is limited, since complete absorption of mid-IR light results with samples greater than 10-15 µm in thickness. In contrast, near-IR light is scattered to a much greater extent than it is absorbed, making tissues relatively transparent to near-IR light, thus allowing the examination of much larger volumes of tissue and the potential for in-vivo studies.

The near-IR region is often sub-divided into the short (680-1100 nm) and long (1100-2500 nm) near-IR wavelengths, based upon the technology required to analyze light in these wavelength regions. At shorter near-IR wavelengths, the heme proteins (oxy- and deoxyhemoglobin and myoglobin) and cytochromes dominate the spectra, and their absorptions are indicative of regional blood flow and oxygen consumption. Long wavelength near-IR absorptions arise from overtones and combination bands of the molecular vibrations of C—H, N—H and O—H groups. The absorption of near-IR light therefore provides information concerning tissue composition (i.e. lipids, proteins) and oxygen delivery and utilization.

Acquisition of visible/near-IR data is straightforward. Visible and near-IR light is brought from a spectrometer to the skin via a fiber optic cable. The light penetrates the skin, and water, hemoglobin species, cytochromes, lipids and proteins absorb this light at specific frequencies. The remaining light is scattered by the skin, with some light being scattered back to the fiber optic probe. The light is collected by the probe and transmitted back to the spectrometer for analysis. A plot of the amount of light absorbed at each wavelength (the spectrum) is computed. Measurements are rapid, non-destructive and non-invasive.

SUMMARY OF THE INVENTION

According to a first aspect of the invention, there is provided a method of diagnosing skin diseases comprising: providing a patient having a disease; emitting a beam of visible/near-IR light into a portion of the skin afflicted with the skin disease; collecting and analyzing reflected light from the beam, thereby producing a condition spectrum; emitting a beam of visible/near-IR light into a control skin portion of the patient which is not afflicted with the skin disease; collecting and analyzing reflected light from the beam, thereby producing a control spectrum; comparing the control spectrum and the condition spectrum; and identifying the skin disease based on said comparison.

According to a second aspect of the invention, there is provided a method comprising:

a) providing a patient having a skin disease;

b) emitting a beam of visible/near-IR light into a portion of the skin afflicted with the skin disease;

c) collecting and analyzing reflected light from the beam, thereby producing a disease spectrum;

d) emitting a beam of visible/near-IR light into a control skin portion of the patient which is not afflicted with the skin disease;

e) collecting and analyzing reflected light from the beam, thereby producing a control spectrum;

f) performing a biopsy on the portion of the skin afflicted with the skin disease;

g) classifying the skin disease based on the biopsy;

h) assigning the control spectrum and the disease spectrum to a skin disease group based on the classification; and i) creating a database by repeating steps (a) to (h).

Figure 1:
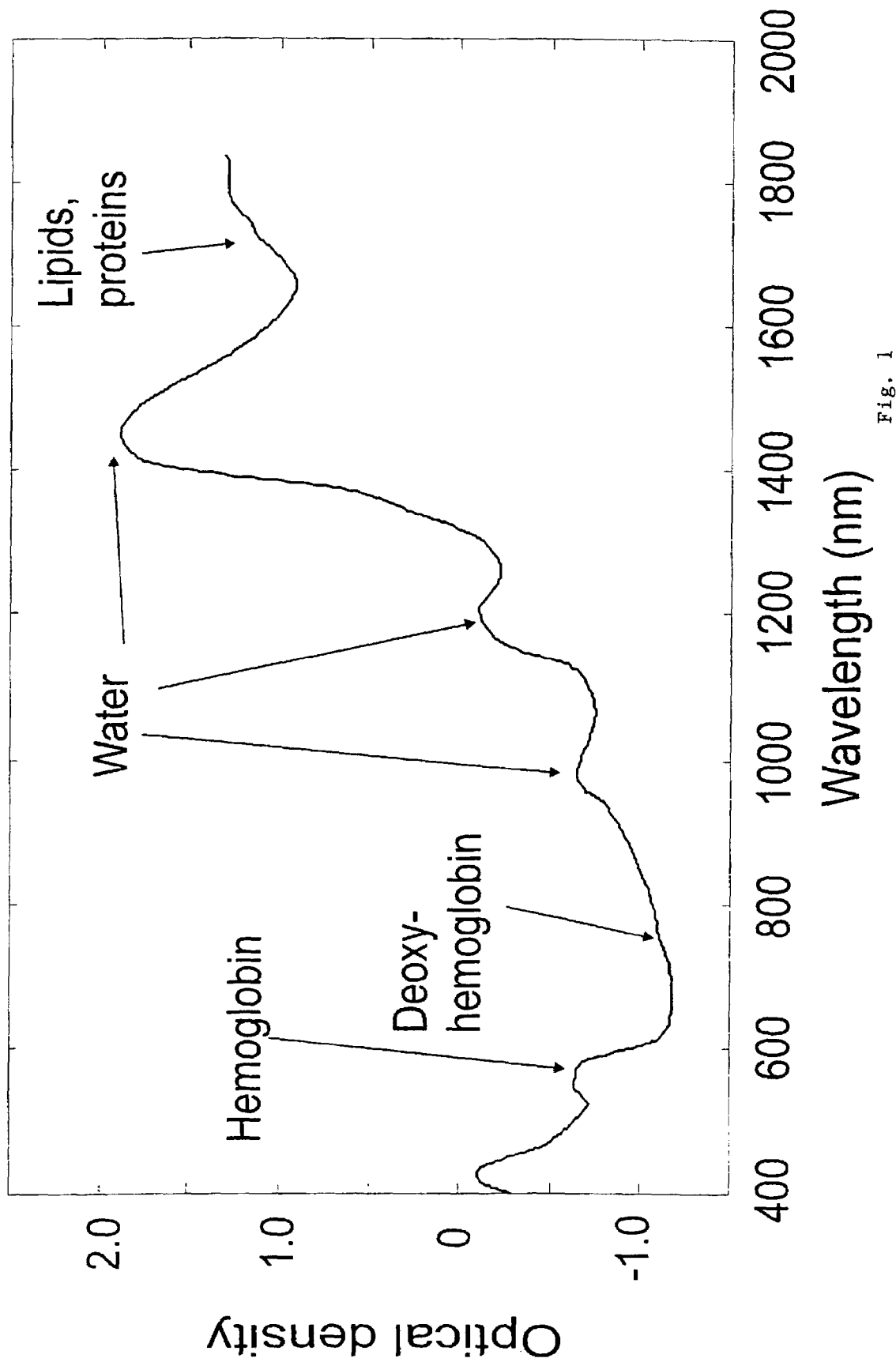
FIG. 1 shows the mean normal control (n=378) and variance spectrum. The origin of the major absorption bands are indicated. The variance is indicated by the shaded region.

indicated in the darkly shaded regions and the regions that were significant by ANOVA indicated in the lightly shaded regions. Three optimal regions were selected for dysplastic vs. banal nevi (a), five regions for actinic keratoses vs. actinic lentigines (b), five regions for actinic keratoses vs. seborrheic keratoses (c) and four regions for BCC vs. seborrheic keratoses (d). No regions were significant by ANOVA for b and c.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

A "skin condition" is a dermatological disorder that manifests as a rash, irritation or dry skin. Examples of skin conditions are psoriasis, hives, eczema, etc.

A "skin lesion" is a circumscribed abnormal area of the skin such as a tumor, nodule or papule.

A "skin disease" is any abnormal area of the skin caused by disease. Skin diseases include both skin conditions and skin lesions (but not injuries due to external insult such as cuts and burns).

"Actinic keratoses" are reddish, rough areas of damaged skin which are considered pre-malignant. A small percentage of these lesions develop into the malignant tumor, squamous cell carcinoma.

"Basal cell carcinoma" or BCC refers to a slow-growing malignant epithelial neoplasm. This type of cancer in usually "cured" by surgical removal if caught early.

"Actinic lentigines" are small benign pigmented lesions often referred to as age or liver spots.

"Dysplastic nevi" refer to atypical moles which are considered to be pre-malignant or at greater risk of becoming malignant.

"Seborrheic keratoses" are common light brown to black skin growths that are benign.

"Banal or benign nevi" are common benign moles.

The purpose of this study was to determine whether the information obtained from visible/near-IR spectroscopy for a variety of skin diseases would prove to be sufficiently characteristic as to be diagnostic. Spectra from six types of skin lesion were collected, and univariate and multivariate techniques were used to determine whether differences existed between the skin lesions.

Specifically, visible/near-IR spectra were recorded for a number of patients having skin lesions, as described below. In addition, a spectrum was taken of an unaffected skin portion as a control from each patient. A biopsy was also performed on the skin lesion and the results of the biopsy were used to assign the skin lesion to a specific category. The disease spectra and the control spectra were then compared using statistical analysis as described below to detect wavelength regions of significant difference between the control spectra and the lesion spectra. These results were then grouped by skin lesion category based on the biopsy results. As discussed below, the grouped spectra showed characteristic patterns in the differential spectra over a specific set of wavelengths. As a consequence, these differences can be used to identify or diagnose a skin disease by comparing the visible/near-IR spectrum of a control region to a spectrum taken of the region of interest.

Specifically, the skin disease is diagnosed by emitting a beam of visible/near-IR light into a portion of the skin afflicted with the skin disease, and collecting and analyzing reflected light from the beam, thereby producing a spectrum of the diseased skin portion. The process is repeated for an unaffected region of skin, thereby providing a control spectrum. The control spectrum and the disease spectrum are then compared and the skin disease is identified based on the comparison.

The skin disease is selected from the group consisting of dysplastic melanocytic nevi; banal nevi; lentigines; actinic keratoses; seborrheic keratoses; basal cell carcinoma; and malignant melanoma.

The control spectrum and the disease spectrum may be compared at wavelengths corresponding to visible/near-IR absorption by oxyhemoglobin, deoxyhemoglobin, water, proteins, lipids or combinations thereof. The wavelengths may be selected from the group consisting of: 518-598 nm; 618-698 nm; 718-798 nm; 918-998 nm; 1158-1238 nm; 1418-1498 nm; 1718-1798 nm; and combinations thereof.

In another embodiment of the invention, spectra are taken of affected and control regions from several patients. A biopsy is then performed on each of the affected region, which is then used to positively identify the skin condition. The spectra are grouped according to skin condition, thereby forming a database. The control spectra and the disease spectra in each skin disease group in the database are then reduced to diagnostic wavelengths using a region selection algorithm. This algorithm is then used to analyze spectra from other skin portions so that the disease afflicting the skin portion can be identified based solely on the spectrum, without performing a biopsy.

EXAMPLE 1—SUBJECT SELECTION

A total of 195 cases were sampled from a study population of 153 (83 women and 70 men) referred to a dermatology clinic for definitive diagnosis of a skin disease, and for whom proper management necessitated a biopsy of their lesion(s). Upon decision by the dermatologist that a biopsy (ies) was required, the patient was referred to the study nurse and the spectrum was recorded. Subjects were excluded from the study if they: 1) were using any skin medication on the site of the lesion, 2) were presently undergoing radiotherapy or chemotherapy, 3) had either Type I or Type II diabetes (which may alter blood flow in the skin). Following an explanation and discussion of the study, informed consent was obtained. Ethical approval for this study was obtained from the Research Ethics Board of the National Research Council of Canada.

EXAMPLE II—ACQUISITION OF SPECTRA

Spectra were recorded in the 400-2500 nm range in 2 nm steps using a commercial spectrometer (Foss NIRSystems Model 6500) equipped with a bifurcated visible/near-IR fiber optic probe with a 7 mm active area. Each reflectance spectrum was collected with a 10 nm slit width, and consisted of 32 scans, which were co-added to improve signal to noise. Prior to obtaining the readings, the subject's skin and the end of the probe were cleansed with 70% alcohol. The fiber optic probe was then positioned 0.5 mm from the measurement site by measuring with a micrometer. For all 195 cases, three (3) visible/near-IR spectra were taken from: 1) the lesion and 2) an area of normal appearing skin (the control site). Acquisition of each spectrum took 40 seconds.

After acquisition of visible/near-IR spectra, a biopsy of the lesion was taken. Biopsies were sent to the pathologist, and hematoxylin and eosin stained sections of formalin fixed, paraffin embedded slides were evaluated. Based on the histopathology, spectra were grouped into one of six lesion categories: 1) actinic keratoses (33 cases, 99 spectra), 2) BCC (32 cases, 96 spectra), 3) dysplastic melanocytic nevi (13 cases, 39 spectra), 4) actinic lentigines (12 cases, 36 spectra), 5) banal common acquired nevi (22 cases, 19 intradermal and 3 compound nevi, 66 spectra) and 6) seborrheic keratoses (18 cases, 54 spectra). A total of 130 cases were thus included in the data set. The remaining 65 cases either did not fit into one of the above categories or the patient declined to have a biopsy after the measurements. The histopathology was the "gold standard" by which spectra were classified.

EXAMPLE III—SPECTRAL PROCESSING AND ANALYSIS

Significant noise was apparent in the 1850-2400 nm region due to the strong absorption of light by water in that spectral range. Prior to data analysis spectra were therefore truncated to 400-1840 nm, leaving a total of 720 data points per spectrum. Spectra were pooled according to the above 6 lesion categories. Spectra were pre-processed by normalizing to their total area and offset correcting.

The mean and standard deviation spectrum for each lesion category was generated by calculating the mean (+/−SD) intensity at each of the 720 spectral data points for each category. Any spectrum that lay outside 2 standard deviations from the mean for each lesion group was removed from the study. It is interesting to note that in all instances spectra that lay outside 2 standard deviations were associated with patient movement as recorded by the study nurse. The remaining spectral database consisted of 94 (of 99) actinic keratosis spectra, 90 (of 96) BCC spectra, 38 (of 39) dysplastic nevus spectra, 33 (of 36) actinic lentigo spectra, 63 (of 66) banal nevi and 49 (of 54) seborrheic keratosis spectra. Mean spectra for individual lesions were then calculated, which resulted in 33 actinic keratoses, 34 BCC, 13 dysplastic nevi, 12 actinic lentigines, 22 banal nevi and 18 seborrheic keratoses spectra.

The same procedure was followed for control spectra. A total of 378 spectra from 390 possible control spectra (acquired from 130 sites) were found to lie within 2 standard deviations of the mean spectrum. Once again, control spectra that lay outside 2 standard deviations from the mean were associated with patient movement. Control spectra for each control site were then averaged, resulting in 130 control spectra.

For each of the six skin lesion categories, paired t-tests (Statistica 5.1. StatSoft, Tulsa, Okla.) were applied to find significant differences between lesion spectra and control skin spectra. The resulting p-values were plotted against wavelength, as discussed below. Subsequently each mean control spectrum was subtracted from each mean lesion spectrum in a pair-wise fashion to emphasize differences between spectra. This resulted in one difference spectrum for each case, representing spectral differences between the lesion and control site. Based upon t-test results, seven regions were selected in which to perform repeated measures analysis of variance (ANOVA) on difference spectra, as discussed below. Fisher's least significant difference (LSD) and Duncan's multiple range tests were performed post hoc (Statistica 5.1, StatSoft), as discussed below.

In addition to univariate statistical tests, data was subjected to multivariate analysis. In the first step of the multivariate analysis, an optimal region selection genetic algorithm (GA-ORS) (Nikulin et al, 1998, *NMR Biomed* 11:209-216) was applied to determine the 3-5 most discriminatory regions of the difference spectra. The data sets were then reduced to only those wavelength regions and linear discriminant analysis (LDA) was performed using a "leave-one-out" cross validation strategy (Eysel et al, 1997, *Biospectroscopy* 3:161-167; Mansfield et al, 1999, *Vib Spectrosc* 19:3345). LDA returns a value ranging between 0 (not belonging) and 1 (belonging) to each spectrum in a data set, indicating the membership in each class. Thus, the values returned provide an indication of the likelihood of a spectrum belonging to each class. Each spectrum is then allocated to the class to which it most belongs.

EXAMPLE IV—RESULTS

The mean control (i.e. from normal skin) visible/near-IR spectrum is shown in FIG. 1. Spectra are plotted showing the amount of light absorbed by the skin at each wavelength between 400-1840 nm. Each peak in the spectrum can be assigned to a specific compound found in the skin. Visually, strong absorption bands arising from O—H groups of water dominate the spectrum. However, much information is present in the weaker spectral features. For instance, the relatively strong absorption feature at ~550 nm arises from hemoglobin species and provides information relating to the oxygenation status of tissues. Further information on tissue oxygenation can be obtained from analysis of a weak absorption feature at 760 nm, arising from deoxyhemoglobin (Stranc et al, 1998, *Br J Plast Surg* 51:210-217). Compositional information can be obtained from an analysis of two absorption bands between 1700-1800 nm associated with C—H groups of skin lipids. In addition, a series of weak absorption bands arising from protein N—H groups is found in close proximity (usually overlapped by) the strong water absorptions. In addition to information on tissue composition (lipid, protein and water content) and tissue oxygenation, information on tissue architecture/optical properties can be obtained from the spectra. Changes in tissue architecture/optical properties may affect the basic nature of the interaction of light with the tissue. For example changes in the character of the epidermis (i.e. dehydration) may result in more scattering of light from the surface, reducing penetration of light into the skin in a wavelength dependant manner. Also, different tumor densities (i.e. nodular vs. diffuse) may result in more scattering of light from the surface. Such phenomena would be manifest in spectra as changes in the slope of the spectral curves, especially in the 400-780 nm region.

The variance observed at each point in each of the spectrum (n=378) (variance spectra) is also plotted in FIG. 1. The variance spectra appear essentially identical in form to the mean spectrum, the major difference being a slight offset. Variance is essentially constant across the spectral range used. This suggests that spectra are highly reproducible, with only slight differences in absorption intensity observed across the spectrum (most likely due to small differences in probe placement).

Figure 2:
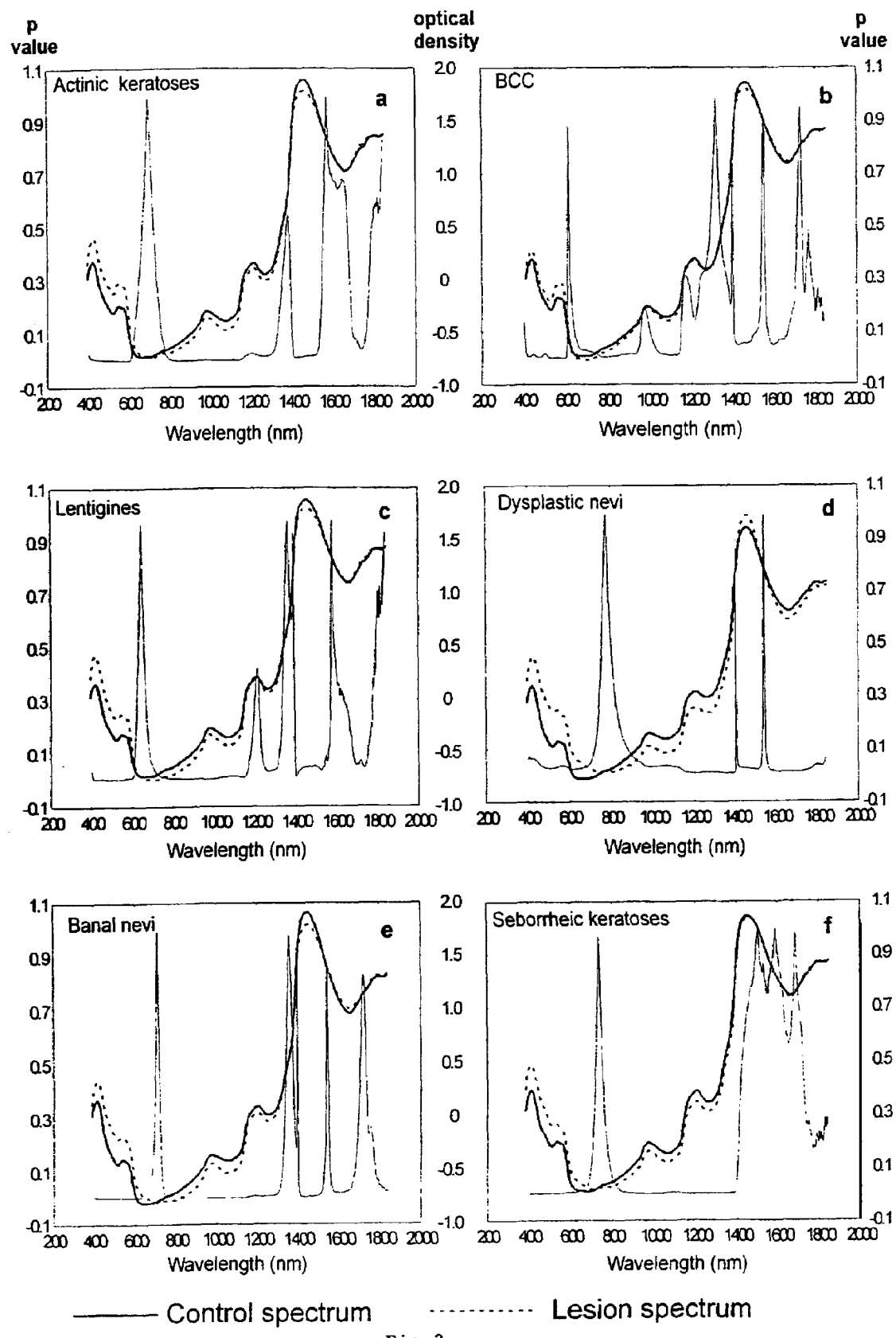
FIG. 2 shows paired t-test results comparing normal and skin lesion near-IR spectra. The mean normalized spectra are shown overlaid on p-plot traces. The optical density scale refers to the spectra, while the p-value scales correspond to the p-plot traces.

Mean spectra for each type of lesion are shown in FIG. 2. No obvious qualitative differences were observed in spectral groups. To assess whether significant differences existed between control and abnormal skin, paired t-tests were applied at each wavelength. The resulting p-values were plotted against wavelength (p-plots). In FIG. 2 mean normalized lesion spectra (red traces) and control spectra (blue traces) are shown overlaid on corresponding p-plots (black traces). Several areas of the resulting p-plot contained contiguous regions of statistically significant p-values ($p<0.05$). Each lesion-normal comparison exhibited a slightly different p-plot, and therefore, a distinct pattern of significance.

Figure 3:
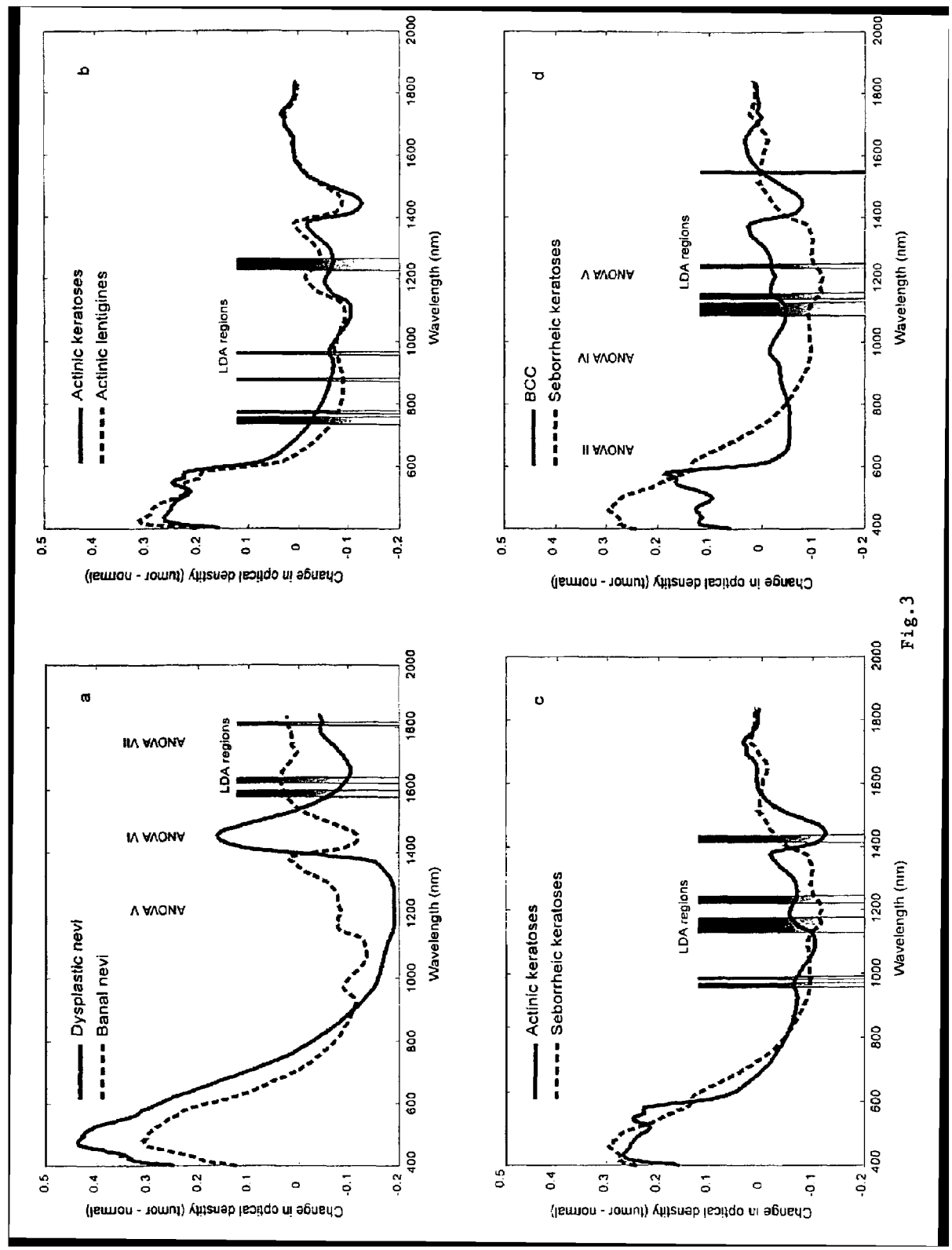
FIG. 3 shows the difference visible/near-IR spectra from skin lesions. Difference spectra were obtained by subtracting each lesion-normal pairing for each group shown in FIG. 2. Dyplastic nevi and banal nevi are shown in FIG. 3a: actinic keratoses and actinic lentigines are shown in FIG. 3b; actinic keratoses and seborrheic keratoses are shown in FIG. 3c; and basal cell carcinoma and seborrheic keratoses are shown in FIG. 3d. The areas used for analysis of variance are shown over the spectra.

Based upon the p-plots, the following regions were chosen in which to perform repeated measures ANOVA on difference spectra: 1) 518-598 nm, 2) 618-698 nm, 3) 718-798 nm, 4) 918-998 nm, 5) 1158-1238 nm, 6) 1418-1498 nm, 7) 1718-1798 nm (shaded regions in FIG. 3). Fisher's LSD and Duncan's Multiple Range tests, multiple comparison tests that are designed to correct for multiple pair-wise comparisons, were performed post-hoc. As shown in Table I, both LSD and Duncan's tests showed various significant inter-group differences between the lesion groups, depending on the region tested. Spectra from dysplastic nevi were significantly different from actinic keratoses, BCC, lentigines, banal nevi and seborrheic keratoses in a number of spectral regions. In addition, BCC spectra were significantly different from banal nevi and seborrheic keratoses in three spectral regions, and seborrheic keratoses were different from lentigines in one spectral region.

Figure 4:
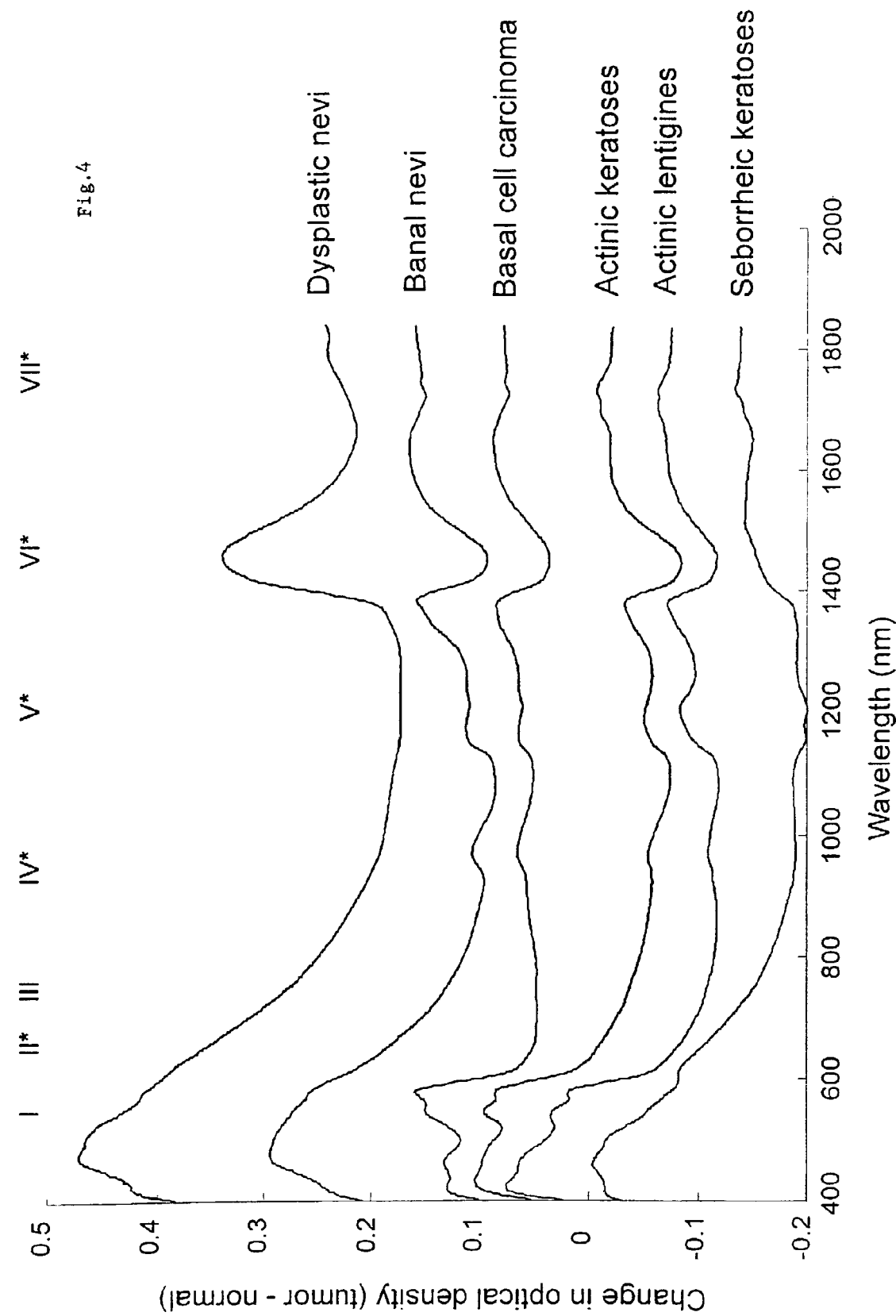
FIG. 4 shows optimal classification regions of visible/near-IR spectra from skin lesions. Class average spectra are shown with the regions for optimal classification (GA-ORS)

Two class LDAs were performed on the following comparisons: 1) dysplastic vs. banal nevi, 2) dysplastic nevi vs. lentigines, 3) actinic keratoses vs. lentigines, 4) actinic keratoses vs. seborrheic keratoses, 5) BCC vs. seborrheic keratoses, 6) BCC vs. banal nevi and 7) dysplastic nevi vs. seborrheic keratoses. Prior to performing the LDA, optimal regions were identified by the GA-ORS algorithm. FIG. 4 shows the optimal regions for comparisons 1, 3, 4 and 5. LDA resulted in an overall accuracy of 97.7-72.4% compared to a clinical accuracy (by visual examination) of 100-78.0% and are shown in Table II. For each comparison in Table II, the numbers in rows represent the histopathological classification, while results in columns represent the calculated classification.

EXAMPLE VI—DISCUSSION

The visible/near-IR spectra of skin presented here exhibit strong absorption bands from water and a number of weak, but consistent, absorption bands arising from oxy- and deoxy-hemoglobin, lipids and proteins. However, visual examination of spectra did not show distinct differences in these spectral features that could be used to distinguish between spectra of skin diseases and healthy skin. Univariate statistics were therefore applied in order to determine whether differences existed between skin lesions and healthy skin. Subsequently, multivariate statistics (LDA) were performed in an attempt to objectively classify spectra.

As control spectra were acquired from a normal site for each lesion, paired t-tests were performed on spectra from each disease grouping. The results demonstrated that each of the skin lesions studied differed significantly from normal skin in a number of contiguous regions in the visible/near-IR region. Although comparisons were only made between each skin lesion group and control skin, each p-plot exhibited a slightly different pattern of significance, suggesting that significant spectral differences existed between the different types of skin lesions.

To assess whether statistical differences did indeed occur between the different types of skin lesions, ANOVA was performed on difference spectra. Fisher's LSD and Duncan's multiple range tests were applied post hoc. Spectral sub-regions were identified for these analyses. Results demonstrated that significant differences existed between spectra of the different types of lesions in all regions tested, except the visible region of the spectrum (region I, 518-598 nm). However, differences in no one spectral region were sufficient to allow differentiation between all of the lesion groups.

Some general comments may be made concerning the nature of the spectral differences identified by univariate statistics. At least two of the spectral regions exhibiting significant differences (by ANOVA) are associated with absorption bands from hemoglobin species. Specifically, the region 718-798 nm contains the absorption of deoxyhemoglobin, while the region 918-998 nm contains a broad absorption associated with oxyhemoglobin. Thus, significant differences between lesion and control spectra in these regions may be indicative of changes in oxygenation or blood flow. The regions 1158-1238 nm and 1418-1498 nm contain significant absorption bands from water, and possibly some contribution from protein N—H groups. Thus, it appears as if changes in the amount or structure of water in tissues occur between some types of lesion and control tissues. Finally, spectral bands attributed primarily to C—H groups of skin lipids populate the region 1718-1798 nm. Significant differences between spectra in this region may imply differences in the amount or structure of skin lipids.

Application of univariate statistics showed that significant differences not only exist between spectra of healthy skin and the six lesions studied, but also between spectra of the lesions. Whilst this is encouraging, significant differences are not necessarily diagnostic differences. To assess whether there were spectral differences with diagnostic value, a pattern recognition technique, genetic algorithm guided linear discriminant analysis (GA-LDA), was applied to the data. GA-LDA makes use of the fact that clinical information is available regarding the spectroscopic data (i.e. biopsy reports). This information is used to train an LDA algorithm to recognize the particular combinations of peak frequencies, absorption bandwidths, relative intensities, etc. that are characteristic of spectra from a particular clinical grouping. The trained LDA algorithm can then be applied to unknown spectra, and the unknown spectra are partitioned into one of the clinical groupings based upon the spectral pattern found. The advantage of LDA is that a combination of spectral regions (which perhaps on their own do not contain sufficient information to allow diagnosis), rather than individual regions, are used to achieve a diagnosis.

Specifically, the genetic algorithm starts at one end of an N-point spectrum by selecting a window consisting of $M<<N$ adjacent data points. Typically, M=10-12. Discriminant analysis is carried out with these M points as local attributes, and the average classification accuracy on the test subsets is recorded. The window is advanced by M/2 data points along the spectrum and the process is repeated. When the spectra are fully traversed, the nonoverlapping subregions are sorted in decreasing order of accuracy. If the best subregion found satisfies a prescribed accuracy (typically>90%), the subregion selection process is terminated. If this does not occur, the next stage is initiated. Typically, the best 6-8 subregions are tested in all possible combinations. The most parsimonious combination that satisfies the accuracy criterion provides the feature set for the final classifier. The linear discriminant analysis program takes the regions selected by the algorithm and identifies the hyperplane that optimally separates the sets of points corresponding to the spectral classes of interest. Specifically, class assignment of any given spectrum involves computing its distance from all class centroids (i.e. the representative class average spectrum) and allocating it to the class whose centroid is nearest. Thus, for each spectrum, a value ranging between 0 (not belonging) and 1 (belonging) is given, indicating the membership in each class, with the sum of the membership values for all classes being unity. The value returned therefore provides an indication of the likelihood of the spectrum belonging to each class. Thus, for spectra arising from BCC, an ideal LDA would return values of 1 for the BCC class and 0 for the other classes in the comparison.

As will be appreciated by one knowledgeable in the art, the above is intended as an illustrative example. Other suitable analytical methods may also be used.

GA-LDA was applied to difference spectra from benign and premalignant/malignant lesion groups. Some of the more difficult visual diagnoses were successfully distinguished. All LDA comparisons save one resulted in an accuracy rate greater than 80%. Although the clinical (visual) diagnostic accuracy rate in this particular study was high (greater than 78%), other studies report clinical diagnostic accuracy rates of 42-65% (Pichter et al, 1991, *Br J Dermatol* 125 (Suppl 38):93-97; Hallock and Lutz, 1998, *Plast Reconstr Surg* 101:1255-1261). The LDA results presented here compare favorably with such studies Spectral regions that contained diagnostic information were not the same as those identified by ANOVA, perhaps reflecting the fact that LDA uses combinations of regions (each of which on it's own may not show significant differences between classes) to enable diagnosis. However, many spectral regions identified by GA-LDA suggest essentially the same biochemical basis for distinguishing between classes as by ANOVA. For example regions around 760 nm (deoxyhemoglobin), 900 nm (oxyhemoglobin) and 1200 nm (water) allowed discrimination between actinic keratoses and actinic lentigines. However, in some cases the biophysical basis underlying the diagnostic regions remains unclear.

The ANOVA and LDA results are both positive steps towards the differential diagnosis of skin cancer. For example, from a clinical perspective, it is particularly noteworthy that dysplastic nevi exhibited a highly significant difference (p<0.001) from almost all other lesion groups across most of the regions tested by ANOVA. In addition, classification between dysplastic and banal nevi had the highest accuracy of all classifications (97.7%), with classification between dysplastic nevi and lentigines close behind (92%). Although there is debate over the propensity of dysplastic nevi to develop into malignant melanoma, the accurate and early diagnosis of dysplastic nevi is a significant development in the recent emphasis placed on melanoma detection. The differentiation of the pre-malignant (Callen et al, 1997, *J Am Acad Dermatol* 36:650-653) actinic keratosis from an early SCC, seborrheic keratosis or lentigo is of clinical import and ANOVA was not successful in this regard. However, LDA differentiated actinic keratoses from lentigines and seborrheic keratoses with an accuracy of 88.9% and 84.3%, respectively. It has been suggested that clinicians focus more on the features of seborrheic keratoses for differential diagnosis of skin cancer (Marks et al, 1997, *J Am Acad Dermatol* 36:721-726), as seborrheic keratosis is perhaps the most common lesion considered in the differential diagnosis of melanoma in older persons (Rivers and Gallagher, 1995, *Cancer* 75:661-666). Our results showed significant differences between seborrheic keratoses, dysplastic nevi, BCC and lentigines by ANOVA.

EXAMPLE VII—CONCLUSIONS

This is the first extensive visible/near-IR spectroscopic study of the non-inflammatory skin lesions most commonly encountered in a general dermatology clinic. The visible/near-IR spectroscopic technique has clear potential for the non-invasive diagnosis of skin diseases, differentiating between normal skin and a variety of common skin lesions. More importantly, it appears that visible/near-IR spectroscopy holds promise for the discrimination of malignant from benign skin tumors.

Visible/near-IR spectroscopy could form the basis of a clinical method to diagnose skin diseases. It is rapid (i.e. acquisition time of minutes), simple to perform and non-invasive. Measurements are accurate and reproducible. Collection of spectra causes little or no patient discomfort, does not alter the basic physiology of the skin, poses no hazard to the patient and does not interfere with any other standard clinical diagnostic practices. The test could be performed by a non-specialist and, therefore, might be a useful tool for pre-screening skin diseases.

While the preferred embodiments of the invention have been described above, it will be recognized and understood that various modifications may be made therein, and the appended claims are intended to cover all such modifications which may fall within the spirit and scope of the invention.

TABLE I

Statistically significant p values (p < 0.05) from Duncan's multiple range and Fisher's least significant difference (LSD) tests for the seven regions tested.

| Region (nm) | Significant comparisons (Duncan's) | p value | Significant comparisons (Fisher's LSD) | p value |
|---|---|---|---|---|
| I. 518-598 | No significance | Not applicable | No significance | Not applicable |
| II. 618-698 | Dysp. nevi vs actinic keratoses | 0.007 | Dysp. nevi vs actinic keratoses | 0.005 |
| | Dysp. nevi vs BCC | 0.001 | Dysp. nevi vs BCC | 0.001 |
| | Dysp. nevi vs lentigines | 0.001 | Dysp. nevi vs lentigines | 0.002 |
| | BCC vs banal nevi | 0.010 | BCC vs banal nevi | 0.001 |
| | BCC vs seborrheic keratoses | 0.005 | BCC vs seborrheic keratoses | 0.001 |
| | Lentigines vs seborrheic kerat. | 0.042 | BCC vs actinic keratoses | 0.021 |
| III. 718-798 | Dysp. nevi vs BCC | 0.014 | Dysp. nevi vs BCC | 0.008 |
| | Dysp. nevi vs lentigines | 0.006 | Dysp. nevi vs lentigines | 0.014 |
| IV. 918-998 | Dysp. nevi vs BCC | 0.010 | Dysp. nevi vs BCC | 0.005 |
| | BCC vs banal nevi | 0.032 | BCC vs banal nevi | 0.006 |
| | BCC vs seborrheic keratoses | 0.047 | BCC vs seborrheic keratoses | 0.018 |
| V. 1158-1238 | Dysp. nevi vs actinic keratoses | 0.005 | Dysp. nevi vs actinic keratoses | 0.003 |
| | Dysp. nevi vs BCC | 0.001 | Dysp. nevi vs BCC | 0.001 |
| | Dysp. nevi vs lentigines | 0.001 | Dysp. nevi vs lentigines | 0.002 |
| | Dysp. vs banal nevi | 0.022 | Dysp. vs banal nevi | 0.026 |
| | Seborrheic keratoses vs BCC | 0.019 | Seborrheic keratoses vs BCC | 0.005 |
| | Seborrheic kerat. vs lentigines | 0.022 | Seborrheic kerat. vs lentigines | 0.032 |
| VI. 1418-1498 | Dysp. nevi vs actinic keratoses | 0.001 | Dysp. nevi vs actinic keratoses | 0.001 |
| | Dysp. nevi vs BCC | 0.001 | Dysp. nevi vs BCC | 0.001 |
| | Dysp. nevi vs lentigines | 0.001 | Dysp. nevi vs lentigines | 0.001 |
| | Dysp. vs banal nevi | 0.001 | Dysp. vs banal nevi | 0.001 |
| | Dysp. nevi vs seborrheic kerat. | 0.002 | Dysp. nevi vs seborrheic kerat. | 0.007 |

TABLE I-continued

Statistically significant p values (p < 0.05) from Duncan's multiple range and Fisher's least significant difference (LSD) tests for the seven regions tested.

| Region (nm) | Significant comparisons (Duncan's) | p value | Significant comparisons (Fisher's LSD) | p value |
|---|---|---|---|---|
| VII. 1718-1798 | Dysp. nevi vs actinic keratoses | 0.001 | Dysp. nevi vs actinic keratoses | 0.001 |
| | Dysp. nevi vs BCC | 0.001 | Dysp. nevi vs BCC | 0.001 |
| | Dysp. nevi vs lentigines | 0.001 | Dysp. nevi vs lentigines | 0.001 |
| | Dysp. vs banal nevi | 0.001 | Dysp. vs banal nevi | 0.001 |
| | Dysp. nevi vs seborrheic kerat. | 0.001 | Dysp. nevi vs seborrheic kerat. | 0.001 |

TABLE II

Linear discriminant analysis (LDA) results.

| | Dysplastic Nevi | Banal nevi | Accuracy by LDA | Accuracy by clinician |
|---|---|---|---|---|
| Dysplastic nevi | 13[a] | 0 | 100 | 91.7 |
| | | | *97.7* | *89.6* |
| Banal nevi | 1 | 21 | 95.5 | 87.5 |
| | Dysplastic Nevi | Actinic lentigines | | |
| Dysplastic nevi | 12 | 1 | 92.3 | 100 |
| | | | *92.0* | *100* |
| Actinic lentigines | 1 | 11 | 91.7 | 100 |
| | Actinic Keratoses | Actinic lentigines | | |
| Actinic keratoses | 31 | 2 | 93.9 | 96.0 |
| | | | *89.9* | *78.0* |
| Actinic lentigines | 3 | 9 | 75.0 | 60.0 |
| | Actinic Keratoses | Seborrheic keratoses | | |
| Actinic keratoses | 31 | 2 | 93.9 | 96.0 |
| | | | *84.3* | *94.4* |
| Seborrheic keratoses | 6 | 12 | 66.7 | 92.8 |
| | BCC | Seborrheic keratoses | | |
| BCC | 31 | 1 | 96.9 | 96.8 |
| | | | *81.8* | *94.8* |
| Seborrheic keratoses | 6 | 12 | 66.7 | 92.8 |
| | BCC | Banal nevi | | |
| BCC | 31 | 1 | 96.9 | 100 |
| | | | *81.5* | *91.1* |
| Banal nevi | 9 | 13 | 59.1 | 82.3 |
| | Dysplastic Nevi | Seborrheic keratoses | | |
| Dysplastic nevi | 8 | 5 | 61.5 | 100 |
| | | | *72.4* | *100* |
| Seborrheic keratoses | 3 | 15 | 83.3 | 100 |

[a]Numbers in rows represent the histopathological classification, while results in columns represent the calculated LDA classification. The numbers in bold are therefore correct classifications. Numbers in bold italics are overall accuracy.

The invention claimed is:

1. A method of diagnosing skin disease comprising:
providing a patient having a skin disease selected from the group consisting of dysplastic melanocytic nevi; banal nevi; lentigines; actinic keratoses; seborrheic keratoses; basal cell carcinoma; and malignant melanoma;
emitting a beam of visible or near-IR light into a portion of the skin afflicted with the skin disease;
collecting and analyzing reflected light from the beam, thereby producing a disease spectrum;
emitting a beam of visible or near-IR light into a control skin portion of the patient which is not afflicted with the skin disease;
collecting and analyzing reflected light from the beam, thereby producing a control spectrum;
comparing the control spectrum and the disease spectrum; and
identifying the skin disease as dysplastic melanocytic nevi; banal nevi; lentigines; actinic keratoses; seborrheic keratoses; basal cell carcinoma; or malignant melanoma based on said comparison, said method of diagnosing skin disease having a rapid acquisition time of minutes.

2. The method according to claim 1 wherein the control spectrum and the disease spectrum are compared at wavelengths corresponding to visible or near-IR absorption by oxyhemoglobin, deoxyhemoglobin, water, proteins, lipids or combinations thereof.

3. The method according to claim 1 wherein the control spectrum and disease spectra are reduced to diagnostic wavelengths by a region selection algorithm.

4. The method according to claim 3 wherein said wavelengths are selected from the group consisting of: 518-598 nm; 618-698 nm; 718-798 nm; 918-998 nm; 1158-1238 nm; 1418-1498 nm; 1718-1798 nm; and combinations thereof.

5. The method according to claim 3 wherein the skin disease is diagnosed by performing multivariate analysis on the diagnostic wavelengths.

6. The method according to claim 1 wherein the control spectrum and the disease spectrum are compared at wavelengths selected from the group consisting of: 518-598 nm; 618-698 nm; 718-798 nm; 918-998 nm; 1158-1238 nm; 1418-1498 nm; 1718-1798 nm; and combinations thereof.

7. The method according to claim 1 wherein the control spectrum and the condition spectra are averaged spectra.

8. The method according to claim 1 wherein the skin disease is diagnosed comparing the control spectrum and the condition spectrum to a database of visible/near-infrared spectra taken from afflicted and control skin portions of individuals having specific skin diseases.

9. The method according to claim 1 wherein the beam is a beam of visible and near-IR light.

10. A method comprising:
a) providing a patient having a skin disease selected from the group consisting of: dysplastic melanocytic nevi; banal nevi; lentigines, actinic keratoses; seborrheic keratoses; basal cell carcinoma, and malignant melanoma;
b) emitting a beam of visible or near-IR light into a portion of the skin afflicted with the skin disease;
c) collecting and analyzing reflected light from the beam, thereby producing a disease spectrum;
d) emitting a beam of visible or near-IR light into a control skin portion of the patient which is not afflicted with the skin disease;

e) collecting and analyzing reflected light from the beam, thereby producing a control spectrum;

f) performing a biopsy on the portion of the skin afflicted with the skin disease;

g) classifying the skin disease as dysplastic melanocytic nevi; banal nevi; lentigines; actinic keratoses; seborrheic keratoses; basal cell carcinoma; or malignant melanoma based on the biopsy;

h) assigning the control spectrum and the disease spectrum to a skin disease group based on the classification; and i) creating a database by repeating steps (a) to (h), characterized in that steps (b) to (e) have a rapid acquisition time of minutes.

11. The method according to claim 10, including step (j) reducing the control spectra and the disease spectra in each skin disease group in the database to diagnostic wavelengths using a region selection algorithm.

12. The method according to claim 10 wherein the beam is a beam of visible and near-IR light.

* * * * *